US008629265B2

(12) United States Patent
Meier et al.

(10) Patent No.: US 8,629,265 B2
(45) Date of Patent: Jan. 14, 2014

(54) METHOD FOR PRODUCING PHOSPHATE-BRIDGED NUCLEOSIDE CONJUGATES

(75) Inventors: Chris Meier, Jork (DE); Saskia Wolf, Hamburg (DE); Svenja Warnecke, Mannheim (DE)

(73) Assignee: Universitaet Hamburg, Hamburg (DE)

( * ) Notice: Subject to any disclaimer, the term of this patent is extended or adjusted under 35 U.S.C. 154(b) by 217 days.

(21) Appl. No.: 13/057,798

(22) PCT Filed: Aug. 6, 2009

(86) PCT No.: PCT/DE2009/001100
§ 371 (c)(1),
(2), (4) Date: Feb. 7, 2011

(87) PCT Pub. No.: WO2010/015245
PCT Pub. Date: Feb. 11, 2010

(65) Prior Publication Data
US 2011/0137023 A1    Jun. 9, 2011

(30) Foreign Application Priority Data

Aug. 8, 2008    (DE) ........................ 10 2008 036 932
Aug. 29, 2008    (DE) ........................ 10 2008 044 914

(51) Int. Cl.
| | |
|---|---|
| C08B 37/00 | (2006.01) |
| C07H 5/04 | (2006.01) |
| C07H 5/06 | (2006.01) |
| C07H 19/00 | (2006.01) |

(52) U.S. Cl.
USPC ..................................... 536/55.3; 536/26.11

(58) Field of Classification Search
None
See application file for complete search history.

(56) References Cited

U.S. PATENT DOCUMENTS 4,906,415 A * 3/1990 Luft et al. ...................... 562/891

OTHER PUBLICATIONS

Warnecke et al. Nucleic Acids Symposium Series No. 52, Sep. 8, 2008, 583-584.*
Kiser et al. Journal of Laboratory Automation 2001 6:99.*
Senese, General Chemistry Online: FAQ: Simple compounds: Why do some compounds absorb water from air? Apr. 17, 2004.*
Wendicke, Neue Synthese von Nucleosiddiphosphatpyranosen mit Hilfe von cycloSal-aktivierten Phosphatdonatoren, Dissertation, 2007.*
Machine translation of p. 12 of Wendicke, Neue Synthese von Nucleosiddiphosphatpyranosen mit Hilfe von cycloSal-aktivierten Phosphatdonatoren, Dissertation, 2007, machine translation obtained Jun. 25, 2013.*
S. Wendicke, S. Warnecke, C. Meier: "Effiziente Synthese von Nucleosiddiphosphat-Glycopyranosen" Angewandte Chemie, vol. 120, 2008, pp. 15223-1525, XP002554866 cited in the application the whole document.
S. Warnecke, C. Meier: "Synthesis of Nucleoside Di-and Triphosphates and Dinucleoside Polyphosphates with cycloSal-Nucleotides" Journal of Organic Chemistry, vol. 74, 2009, pp. 3024-3030 XP002554867 the whole document.
S. Wolf, T. Zismann, N. Lunau, C. Meier: "Reliable Synthesis of Various Nucleoside Diphosphate Glycopyranoses" Chemistry A European Journal, vol. 15, 2009, pp. 7656-7664 XP002554868 the whole document.
C. Meier: "cycloSal Phosphates as Chemical Trojan Horses for Intercellular Nucleotide and Glycosylmonophosphate Delivery—Chemistry meets Biology" European Journal of Organic Chemistry, 2006, pp. 1081-1102 XP002554869 the whole document.
C. Meier, U. Goerbig, C. Mueller, J. Balzarini: "cycloSal-PMEA and CycloAmb-PMEA: Potentially New Phosphate Prodrugs based on the cycloSal-Pronucleotide Approach" Journal of Medicinal Chemistry, vol. 48, 2005, pp. 8079-8086, XP002554870 the whole document.
Thomann, Jens Oliver, Diastereselektive Synthese von cycloSal-Nucleotiden URN: urn:nbn:de:gbv:18-36640 URL: http://www.sub.uni-hamburg.de/opus/volltexte/2008/3664/ University of Hamburg, 2008 English Abstract Attached.
International Preliminary Report on Patentability Dated Feb. 2, 2011.
Valentin Wittmann, et al. "1H-Tetrazole as Catalyst in Phosphomorpholidate Coupling Reactions: Efficient Synthesis of GDP-Fucose, GDP-Mannose, and UDP-Galactose" The Scripps Research Institute, Department of Chemistry, La Jolla, California J. Org. Chem, 1997, vol. 62, No. 7, pp. 2144-2147.
Prof. P. Kosma, et al. "Efficient Chemical Synthesis of the Two Anomers of ADP-L-glycero- and D-glycero-D-manno-Heptopyranose Allows the Determination of the Substrate Specifities of Bacterial Heptosyltransferases"; Angew.Chem. 2000, 112, No. 22, pp. 4322-4325; Angew. Chem. Int. Ed. 2000, 39, No. 22, pp. 4150-4153 Wiley-VCH Verlag GmbH, D-69451 Weinheim, Germany.
Zofia Milewska, et al. "Quantitative Paper Chromatography of Ribonucleoside Mono-, Di-, and Triphosphates Adapted for Control of Purity of Their Preparations" Analytical Biochemistry 57, 1974, pp. 8-13, Academic Press, Inc. Laboratory of Molecular Biology, Scientific Research Center, The Medical Academy, Lodz, Poland.
Masaharu Yoshikawa, et al. "A Novel Method for Phosphorylation of Nucleosides to 5'-Nucleotides" Central Research Laboratories, Ajinomoto Company Inc., Suzuki-cho, Kawasaki, Japan Tetrahedron Letters No. 50, pp. 5065-5068, 1967 Pergamon Press Ltd., printed in Great Britain.
J. Ludwig "A New Route to Nucleoside 5'-triphosphates" Institute of Biophysics, Biological Research Centre, Hungarian Academy of Sciences, Szeged, Hungary Acta Biochim, et Biophys. Acad. Sci. Hung. 1981, vol. 16, pp. 131-133.
Jerry L. Ruth, et al. "Nucleoside Analogues with Clinical Potential in Antivirus Chemotherapy" Department of Pharmacology, School of Medicine, and Drug Development Program, Cancer Research Center, University of North Carolina, Chapel Hill, North Carolina 27514 Molecular Pharmacology, 20: pp. 415-422, 1981.

(Continued)

*Primary Examiner* — Layla Bland
(74) *Attorney, Agent, or Firm* — Patent Central LLC; Stephan A. Pendorf

(57) ABSTRACT

The invention relates to a method for producing phosphate-bridged nucleoside conjugates. In the method a nucleophile is first dissolved in a non-aqueous solvent and dried, and a cyclosaligenyl phosphate compound is subsequently added to the solution.

10 Claims, 2 Drawing Sheets

(56) References Cited

OTHER PUBLICATIONS

Walter Feldmann "Die Phenolyse des Trimetaphosphats. Über das Monophenyltriphosphat" Institut for Anorganical Chemistry of the German Academie of Science, Berlin, Germany, 1966, 99 (10), pp. 3251-3259.

A. W. Schwartz Specific Phosphorylation of the 2'- and 3'- Positions in Ribonucleosides Department of Exobiology, University of Nijmegen, Nijmegen, Netherlands Chemical Communications, 1969, p. 1393.

J. Ludwig "A Simple One Flask Synthesis of Nucleoside 5'-Triphosphates From Unprotected Nucleosides Via Nucleoside 5'Cyclotriphosphates" Institute of Biophysics, Biological Research Centre Hungarian Academy of Sciences, Hungary Bioact. Mol. 1987, 3, pp. 201-204.

Weidong Wu, et al. "A Combination Chemical and Enzymatic Approach for the Preparation of Azole Carboxamide Nucleoside Triphosphate"; Department of Medicinal Chemistry and Molecular Pharmacology, Purdue University, and Walther Cancer Institute Indiana; J. Org Chem., 2003, 68, pp. 3860-3865.

Teréz Kovács, et al. "Simple Synthesis of 5-Vinyl- and 5-Ethynyl-2'-Deoxyuridine-5'-Triphosphates" Central Research Institute for Chemistry of the Hungarian Academy of Sciences, Budapest, Hungary Tetrahedron Letters, 1988, vol. 29, No. 36, pp. 4525-4528, printed in Great Britain.

William H. Dawson, et al. "The Phosphorylation of Unprotected Nucleosides. Nonselectivity of Phosporous Oxychloride in Trialkylphosphate" Department of Chemistryh University of South Carolina, Columbia, South Carolina J. Carbohydrates Nucleosides Nucletides, 1977, 4(6), pp. 363-375.

S. Roseman, et al. "Nucleoside Polyphosphates. XI. An Improved General Method for the Synthesis of Nucleotide Coenzymes. Syntheses of Uridine-5', Cytidine-5' and Guanosine-5' Diphopsphate Derivatives" J. Am. Chem. Soc. 1961, 83, pp. 659-663.

J. G. Moffatt, et al. "Nucleoside Polyphosphates. VIII. New and Improved Syntheses of Uridine Diphosphate Glucose and Flavin Adenine Dinucleotide Using Nucleoside-5' Phosphoramidates2" J. Am. Chem. Soc. 1954, 80, pp. 3756-3761.

J. Tomasz, et al. "Chemical Synthesis of 5'-pyrophosphate and triphosphate derivatives of 3'-5' ApA, ApG, GpA and GpG. CD Study of the effect of 5'-phosphate groups on the conformation of 3'-5' GpG" Inst. Biophys. Biol. Res. Cent., Hungarian Acad. Sci., Inst. Org. Chem., Hungary, et al. J. Nucleic Acids Research, 1978, vol. 5, No. 8, pp. 2945-2957.

A. Simoncsits, et al. "Nucleoside 5'-phosphordiamidates, synthesis and some properties" Institute of Biophysics, Biological Research Center, Hungarian Academy of Sciences, H-6701, Szeged, Hungary J. Nucleic Acids Research, 1975, vol. 2, No. 7, pp. 1223-1233.

Donald E. Hoard, et al. "Conversion of Mono- and Oligodeoxyribonucleotides to 5'-Triphosphates" Contribution from the Biomedical Research Group, Los Alamos Scientific Laboratory, University of California, Los Alamos, New Mexico Journal of the American Chemical Society, 1965, 87, pp. 1785-1788.

Masamitsu Shimazu, et al. "Facile Synthesis of Nucleotides Containing Polyphosphates by Mn(II) and Cd(II) Ion-Catalyzed Pyrophosphate Bond Formation in Aqueous Solution" Department of Chemistry, Faculty of Engineering, Gunma University, Kiryu, Gunma 376 Japan Tetrahedron Letters, 1990, vol. 31, No. 2, pp. 235-238.

Janos Ludwig, et al. "Rapid and Efficient Synthesis of Nucleoside 5'-O-(1-Thiotriphosphates), 5'-Triphosphates and 2', 3'-Cyclophosphorothioates Using 2-Chloro-4H-1,3,2-benzodioxaphosphorin-4-one" Max-Planck Institut für Experimental Medicine, Göttingen, Germany J. Org. Chem. 1989, 54, pp. 631-635.

Chris Meier, et al. "cycloSal-d4TMP Pronucleotides-Structural Variations, Mechanistic Insights and Antiviral Activity" Institute of Organic Chemistry, University of Hamburg, Germany; Rega Institute for Medical Research, Katholieke Universiteit Leuven, Belgium Current Topics in Medicinal Chemistry 2002, 2, pp. 1111-1121.

Wendicke, S. et al: "Efficient Synthesis of Nucleoside Diphosphate Glycopyranoses" Angewandte Chemie, Int. Ed. 2008, 47, pp. 1500-1502 2008 Wiley-VCH Verlag GmbH & Co. KGaA, Weinheim, Germany.

Wendicke S.: "Neue Synthese von Nucleosiddiphosphatpyranosen mit Hilfe von cycloSal-aktivierten Phospatdonatoren" Doctoral Thesis, presented to the Department of Chemistry, University of Hamburg, Germany, 2007 English language summary attached.

Christie S. M. H., et al: "Syntheses of P1P2-Diadenosine-5' and P1P2-Diuridine-5' Pyrophosphates" Nucleotides. Part XXII. 1953, pp. 2947-2953 University Chemical Laboratory, Cambridge.

\* cited by examiner

METHOD FOR PRODUCING PHOSPHATE-BRIDGED NUCLEOSIDE CONJUGATES

The invention relates to a method for producing phosphate-bridged nucleoside conjugates, in particular of nucleoside diphosphate sugars, (poly)phosphorylated nucleosides, dinucleoside polyphosphates, nucleotide sugar conjugates and nucleoside phosphonates.

Phosphate-bridged nucleoside conjugates are of great importance in nature. They are not only significantly involved in metabolism energy processes, but act as metabolites in almost all biosyntheses. Only a few examples are drawn on to illustrate the immense significance of phosphate groups in natural products.

Dinucleoside polyphosphates play an essential role as signalling and regulatory molecules in various biological functions. Compounds such as diadenosine tetraphosphate (Ap$_4$A) (shown below)

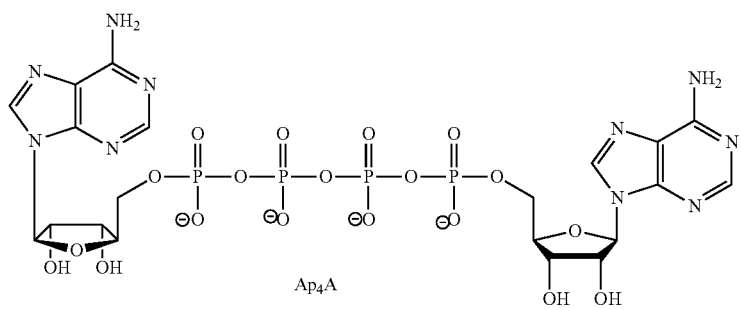

Ap$_4$A and related compounds exhibit high diabetic potential. For example the development and production of chemically stable analogues with the significance of gluconeogenesis, glucose uptake, lipid metabolism and blood pressure regulation in mind therefore is of great interest. For example compounds such as nicotinamide adenine dinucleotide (NAD) or flavin adenine dinucleotide (FAD) are important coenzymes which are critically involved with cellular respiration as hydrogen carriers.

Also, so-called Nucleoside diphosphate or XDP sugars, a specific class of carbohydrate derivatives, are highly important. A general formula for such sugars is shown below:

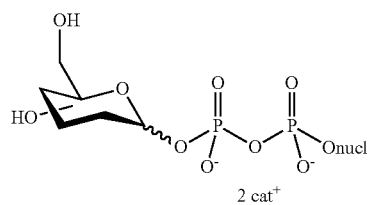

2 cat$^+$

Nucl stands for nucleoside whilst cat$^+$ stands for a cation. These compounds, generally also known as sugar nucleotides, consist of a nucleoside which is bridged via a pyrophosphate unit to a pyranose derivative via the anomeric centre. The anomeric phosphate ester groups of nucleoside diphosphate pyranoses activate the glycosyl residue for enzymatic transfer reactions, whilst the nucleoside residue acts as an additional identifying feature for specific reactions of glycosyl transferases or isomerases. These activated monosaccharides fulfil two functions which are essential for the anabolic metabolism. They are thus involved with the biosynthesis of deoxy sugars, aminodeoxy sugars and branched-chain sugars. Furthermore, XDP sugars are decisive components for the biosynthesis of oligosaccharides and for the majority of the polysaccharides.

Owing to the high biological importance of sugar nucleotides, numerous syntheses of this class of compounds have been published. However, the enzymatic and chemoenzymatic methods are only to be taken into account for the synthesis of natural sugar nucleotides in which the corresponding enzymes are available. Even if this prerequisite is satisfied, the drawbacks still remain that the cost is sometimes high and only small amounts are prepared. The purely chemical syntheses are generally carried out with poor yields of only 5-30%. The few exceptions (V. Wittmann, C.-H. Wong, J. Org. Chem. 1997, 62, 2144-2147; P. Kosma, H. Brade, M. Puchberger, C. Oertelt, S. Gronow, A. Zamyatina, Angew. Chem. 2000, 112, 4322-4325; Angew. Chem. Int. Ed. 2000, 39, 4150-4153) which achieve very good yields with only small modifications to the morpholidate reaction are rarely reproducible. A new, simple and reliable synthesis route for preparing XDP sugars is therefore desirable.

The naturally occurring ribonucleoside triphosphates and deoxyribonucleoside triphosphates (NTPs and dNTPs) are to be used as a final example. They represent the fundamental components for enzyme-catalysed RNA and DNA synthesis in vivo and in vitro, whilst their analogues exhibit enormous potential as inhibitors in many biological processes (for example processes in which DNA polymerases are involved) or as chemotherapeutics. For this reason there is a particularly high interest in synthetic access to these compounds.

However, not only the synthesis of nucleoside triphosphates but also particularly the isolation thereof is highly problematic. By reacting highly charged reagents, such as pyrophosphate, with lipophilic protected nucleoside derivatives, the preparation of these compounds is considerably impaired on the one hand, and on the other the isolation of a charged, water-soluble product from a mixture of hydrophilic and hydrophobic constituents is very difficult. In addition, nucleoside triphosphates are sensitive to hydrolysis owing to their energy-rich anhydride bonds. Their stability depends both on the counterion and on the pH level of the medium (Z. Milewska, H. Panusz, Anal. Biochem. 1974, 57, 8-13).

A range of methods for preparing this class of compound can be found in the prior art. The most frequently used synthesis strategy for the chemical preparation of nucleoside triphosphates is based on the nucleophilic attack of a pyrophosphate salt on an activated nucleoside monophosphate (M. Yoshikawa, T. Kato, T. Takenishi; Tetrahedron Lett 1967, 50, 5065-68). Pyrophosphate salts such as tris-(tetra-n-butylammonium)hydrogen pyrophosphate are commercially available although the activated nucleotides always have to be synthesised.

The nucleoside phosphorochloridates traced back to M. Yoshikawa et al (see above) have been reacted directly with bis(tri-n-butylammonium)pyrophosphate by Ludwig (J. Ludwig; Acta. Biochim, et Biophys. Acad. Sci. Hung. 1981, 16, 131-133.) and others (L. Rutil; Y. C. Cheng, Mol. Pharmacol. 1981, 20, 415-422). The nucleophilic attack of the pyrophosphate ion leads to the formation of the cyclic trimetaphosphate alkyl intermediate (W. Feldmann; Chem. Ber. 1966, 99(10), 3251-3259; A. W. Schwartz; J. Chem. Soc., Chem. Commun. 1969, 1393. Ludwig; Bioact. Mol. 1987, 3, 201-204), which supplies the nucleoside triphosphate in the subsequent hydrolysis step.

However, this method is limited to nucleoside derivatives that are not sensitive to the conditions of monophosphorylation according to M. Yoshikawa, which means it is only possible to use modified purine nucleosides in particular in a very restricted manner (W. Wu, D. E. Bergstrom, V. J. Davisson, J. Org. Chem. 2003, 68, 3860-3865). For example alkene functionalised nucleosides also cannot be phosphorylated in this way since the HCl formed during the reaction from P(O)Cl$_3$ is added to the alkene function (T. Kovács. L. Ötvös.; Tetrahedron Lett. 1988, 29, 4525-4528). In addition, further problems are encountered as a result of the lack of selectivity of P(O)Cl$_3$ as a phosphorylation reagent (W. H. Dawson, R. L. Cargill, R. B. Dunlap, J. Carbohydr. Nucleosides Nucleotides 1977, 4, 363-375).

Further synthesis pathways for nucleoside triphosphates utilised intensively in the prior art use nucleoside phosphoromorpholidates (S. Roseman, J. J. Distler, J. G. Moffatt, H. G. Khorana; J. Am. Chem. Soc. 1961, 83, 659-663; J. G. Moffatt, H. G. Khorana; J. Am. Chem. Soc. 1954, 80, 3756-3761.), -amidates (J. Tomasz, A. Simoncsits, M. Kajtar. R. M. Krug, A. Shatkin, J. Nucl. Acids Res. 1978, 5, 2945-2957; A. Simoncsits, J. Tomasz, J. Nucl. Acids Res. 1975, 2, 1223-1233) or -imidazolidates (D. E. Hoard, D. G. Ott, J Am. Soc. Chem. 1965, 87, 1785-1788; M. Shimazu, K. Shinozuka, H. Sawai, Tetrahedron Lett. 1990, 31, 235-238) as activated nucleotides. However, the reaction to form triphosphate often takes a few days and the chemical yields are rather moderate in many cases. With these methods bis(tri-n-butylammonium)pyrophosphate also displaces the morpholine, amine or imidazole residue from the 5'-nucleosyl phosphate derivative by a nucleophilic substitution.

A further means for synthesis of nucleoside 5'-triphosphates is based on the use of activated nucleoside 5'-phosphites or -phosphoramidites. Works on this topic by J. Ludwig and F. Eckstein were published at an early stage (J. Ludwig, F. Eckstein, J. Org. Chem. 1989, 54, 631-635) in which nucleosides were reacted with a salicylic acid phosphorochloridite to form reactive nucleoside 5'-phosphites which then react in situ with bis(tri-n-butylammonium)pyrophosphate initially to form a cyclic intermediate. The subsequent oxidation/hydrolysis supplies the corresponding triphosphate. An advantage of this synthesis route lies in the greater reactivity of P(III) reagents. However, a drawback is the hydrolysis/oxidation step required starting from the intermediate.

A means for synthesis of nucleoside diphosphate (NDP) sugars with the use of so-called cyclosaligenyl(cycloSal)-nucleoside phosphate triesters has been described by Wendicke et al. (Angew. Chem. 2008, 120, 1523-1525). These cycloSal-nucleoside phosphate triesters, which are also termed cycloSal-NMPs, cycloSal-nucleotides or cycloSal-triesters, are cyclic phosphate triester derivatives in which a salicyl alcohol is cyclically esterified twice with a nucleoside monophosphate. The basic structure of the cyclosaligenyl-nucleotides used by Wendicke et al is shown below.

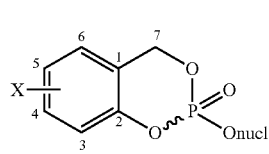

(IIa)

In the method the cycloSal-triester 5-nitro-cycloSal-3'-O-acetyl-thymidine monophosphate was mixed with corresponding glycopyranosyl-1-phosphates in anhydrous DMF at a molar ratio of 1:1.2. The resultant NDP sugars were obtained after 3-5 h at room temperature in yields of 40-60%.

The object of the present invention is to provide a method for the production of phosphate-bridged nucleotide bioconjugates, in particular of nucleoside diphosphate sugars, (poly)phosphorylated nucleosides, dinucleoside polyphosphates, nucleoside phosphonates and nucleotide sugar conjugates, which can be applied within a wide area and supply maximum yields of the compounds as simply and rapidly as possible.

The object is achieved by the method disclosed in claim 1. Preferred embodiments are disclosed in the dependent claims.

In this instance 'phosphate-bridged nucleoside conjugates' are understood to mean compounds of the general formula (I)

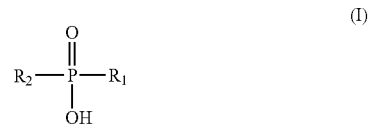

(I)

or salts thereof, wherein $R_1$ is Onucl or nucl and wherein nucl is a nucleoside, nucleoside analogue or a compound of the general formula (III)

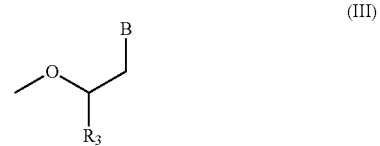

(III)

In compound (III) B is a heterocycle, preferably a nitrogen-containing heterocycle. B is particularly preferably a heterocyclic organic base, preferably a nitrogen-containing heterocyclic organic base, and $R_3$ is selected from the group consisting of H, CH$_2$OH, alkyl or aryl. $R_2$ is any organic compound or phosphate or pyrophosphate, or a residue thereof. $R_2$ is preferably a compound occurring in a living cell or a compound analogous thereto or a corresponding compound residue, for example an alcohol, a sugar, a lipid, a nucleoside, a nucleoside dimonophosphate, nucleoside diphosphate or nucleoside triphosphate, phosphate or pyrophosphate or an alcohol residue, sugar residue, lipid residue, nucleoside residue, nucleoside monophosphate residue, nucleoside diphosphate residue, nucleoside triphosphate residue, phosphate residue or pyrophosphate residue. In this instance reference is also made to bioconjugates.

It has surprisingly been found that phosphate-bridged nucleoside conjugates are obtainable in very high yields in a simple manner if the above-described 'cycloSal concept' is modified in an inventive manner. In the method according to the present invention a compound of the above general formula (I) is produced in which a nucleophile identical to $R_2$ or comprising $R_2$ is first dissolved in a non-aqueous solvent before a compound corresponding to the general formula (II)

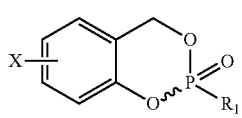

(II)

is added to the solution, under the proviso that the nucleophile is not $H_2O$ or $OH^-$. X can be any electron acceptor and is preferably H, OMe, $MeSO_2$, ketone, =O, C=O, COOH, formyl, ester, $NO_2$ or halogen, where Me stands for methyl. If a carbonyl group C=O is present in the residue X it is preferred for this to be positioned directly on the aromatic ring. The aromatic ring in compound (II) can be substituted once or more with X, wherein the substituents X can be the same or different in the case of multiple substitution. $R_1$ is as defined above. The compound corresponding to formula (II) can also be substituted on C atom 7 (see formula IIa for numbering), for example by methyl, i-propyl, tert-butyl or other alkyl substituents. The aromatic ring may also optionally comprise substituents other than X, for example alkyl or aryl substituents.

It has been found, also surprisingly to the person skilled in the art, that the sequence in which the cycloSal-triester and the nucleophilic compound are combined has an advantageous effect on the success of the synthesis. For example yields of 75-90% have thus been obtained in the case of nucleoside diphosphate sugars with the method according to the invention, that is to say considerably greater yields than those reported by Wendicke et al (Angew. Chem. 2008, 120, 1523-1525).

Furthermore, not only nucleoside diphosphate glycopyranoses but also any other phosphate-bridged nucleoside conjugates can be produced with the method according to the invention. For example nucleoside diphosphates and nucleoside triphosphates could be produced with the use of phosphate and pyrophosphate salts. Very good yields of 55-75% were also obtained in this instance. Nucleoside analogues therefore also can be produced advantageously with the method according to the invention and can be used, for example, as 'prodrug'. 'Prodrugs' are active agent precursors which only release the actual active agent later by splitting off masking groups.

Nucleoside phosphonates can also be produced with the method. These have the general formula

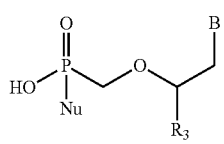

(IV)

wherein B is any heterocycle, preferably a heterocyclic organic base, more preferably a nitrogen-containing heterocyclic base. Nu is as defined above, i.e. a nucleophile. $R_3$ can be selected, for example, from the group consisting of H, $CH_2OH$, alkyl, for example methyl, or aryl. Such nucleoside phosphonates can be analogous in structure to nucleoside compounds, i.e. analogous to nucleosides, and therefore play an important role as chemotherapeutics. Examples of such nucleoside phosphonates are 9-[2-phosphonylmethoxyethyl]adenine (PMEA; Adefovir), (R)-9-[2-phosphonylmethoxypropyl]adenine (PMPA; Tenofovir) and (S)-9-[3-hydroxy-2-phosphonylmethoxypropyl]-cytosine (HPMPC; Cidofovir, Vistide®). They are used, for example, in HIV infections owing to their antiviral effect. For example XDP sugar analogues can be produced with sugars as a nucleophile, corresponding triphosphates with phosphate or pyrophosphate as a nucleophile. Other nucleophiles as described here, for example lipids, can also be used to produce the phosphonates and to produce nucleoside compounds.

Dinucleoside polyphosphates corresponding to the general formula (V)

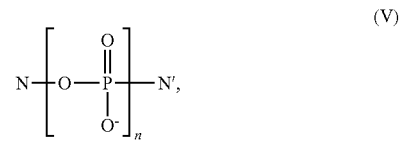

(V)

abbreviated $Np_nN'$, can also be produced in an advantageous manner. In this instance N and N' stand for nucleoside or a nucleoside analogue, wherein N and N' can be the same or different. P stands for phosphate, the subscript n gives the number of interlinked phosphate residues and is preferably 2, 3 or 4. An example of a dinucleoside polyphosphate is diadenosine tetraphosphate ($Ap_4A$), as already mentioned above. NAD or FAD are also dinucleoside polyphosphates within the meaning of the present invention.

It has also been possible for the first time to successfully produce sugar nucleotide bioconjugates with the aid of the method according to the invention.

'Organic compounds' are all compounds having bonds of carbon with carbon and with other elements (with the exception of carbon dioxide, carbon monoxide, carbonic acid and carbonates thereof as well as cyanides, isocyanides, cyanates and isocyanates of metals). Examples of organic compounds include hydrocarbons, i.e. compounds of carbon and hydrogen, alcohols, aldehydes, ketones, carboxylic acids, amines, amides, nitro compounds, nitriles, alkanethiols, sulphides, sulphates, phosphates, phosphines, organometallic compounds, aliphatic hydrocarbons, acyclic hydrocarbons, saturated (alkanes), unsaturated (alkenes and alkynes), cyclic hydrocarbons, simple or condensed aromatic hydrocarbons (aromates), heterocycles, biochemical compounds (amino acids, proteins, nucleosides, nucleotides, carbohydrates, lipids), etc.

A 'heterocycle' is a cyclic compound with ring-forming atoms of at least two different chemical elements. In particular, the term is understood to mean an annular organic compound, in the ring structure of which at least one carbon atom is replaced by another element, i.e. a heteroatom, for example is replaced by nitrogen, oxygen and/or sulphur. A ring structure can consist of one or more interconnected rings and can contain one or more identical or different heteroatoms.

The term 'nucleophile' is known to the person skilled in the art and, in this instance, has the meaning familiar to the person skilled in the art. In particular in this instance, a nucleophile is to be understood to be a molecule which contains a negatively polarised region, a negatively polarised functional group or a free electron pair, generally in an energy-rich orbital. The term also includes molecules which are nucleophilic in relation to a considered reaction partner or to a region of the reaction partner, i.e. is relatively rich in electrons. The reaction partner is also referred to as an electrophile since it takes on electrons from the nucleophile. Nucleophiles can form covalent bonds by providing electrons to a reaction partner. The electrons required for the bond generally originate only from the nucleophile. Nucleophiles can be negatively charged (anions). Examples of typical nucleophilic reagents include carbanions, anions, Lewis bases, aromates, alcohols, amines and compounds with olefinic double bonds.

The strength of nucleophilicity depends, for example, on the reaction partner, the alkalinity, the solvent and steric factors. The factors that influence the nucleophilicity of a compound are well known to the person skilled in the art and he can therefore easily determine the nucleophilic properties of a compound. The nucleophilicity of a molecule is advantageously based on the strongest nucleophilic atom or on the strongest nucleophilic functional group.

In the case of the cycloSal-phosphate triester corresponding to the general formula (II) above and used as an electrophile, the electrophilicity of the phosphorous atom can be controlled by the substituents X on the cycloSal-aromates (see C. Meier, J. Renze, C. Ducho, J. Balzarini, Curr. Topics in Med. Chem. 2002, 2, 1111-1121, the disclosure of which is incorporated herein fully by reference). The electrophilicity is reduced by the introduction of donor substituents on the aromatic ring, whilst in contrast acceptor substituents increase the reaction rate of the initial reaction, i.e. the cycloSal ring opening.

An 'electron acceptor' is a compound, a region of a compound or a functional group which takes on electrons and thus causes a shift in the charge, i.e. a polarisation, of a compound. Examples of electron acceptor groups include OMe, $MeSO_2$, =O, COOH, ketones and the keto group, formyl, esters and the ester group, $NO_2$ and halogen (for example F, Cl, Br, I). Me stands for methyl. Preferred esters as electron acceptors are those in which the ester group is positioned as close as possible to and preferably directly on the aromatic ring. Preferred ketones as electron acceptors are those in which the keto group is positioned as close as possible to and preferably directly on the aromatic ring.

Esters are compounds which contain the ester group R'—COO—R", where R' and R" can be any substituted or non-substituted, branched-chain or straight-chain hydrocarbon residues, for example alkyl residues or aryl residues.

Ketones are compounds which contain the keto group R'—CO—R", where R' and R" can be any substituted or non-substituted, branched-chain or straight-chain hydrocarbon residues, for example alkyl residues or aryl residues.

As used herein a 'nucleoside' is understood to mean organic molecules which consist of a sugar residue and an organic base, for example a heterocyclic organic base, in particular a nitrogen-containing heterocyclic organic base. The sugar residue is generally a pentose, for example deoxyribose or ribose, but can also be another sugar. A 'nucleobase' is understood to mean organic bases which occur in RNA or DNA. Nucleobases are often purines (R) and pyrimidines (Y). Examples of purines include guanine (G) and adenine (A). Examples of pyrimidines include cytosine (C), thymine (T) and uracil (U). Phosphorylated nucleosides, for example nucleoside monophosphates (NMPs), nucleoside diphosphates (NDPs) and nucleoside triphosphates (NTPs) are also referred to as nucleotides. The phosphate, diphosphate (pyrophosphate) or triphosphate group is generally linked to the 5'-C atom of the sugar component of the nucleoside, but for example can also be linked to the 3'-C atom.

As used herein a 'nucleoside analogue' is understood to mean a compound that does not occur naturally in the human body, but is so structurally similar to a nucleoside that does occur naturally in the human body that, for example, it is processed by the cells and/or by viral enzymes in a manner substantially corresponding to that of a natural nucleoside, for example is phosphorylated and incorporated in a RNA or DNA strand. A nucleoside analogue can even be a nucleoside. However, for example it may also be another compound having the above properties, for example a compound formed of a heterocyclic base and a residue which is not a sugar. Examples of nucleoside analogues include, for example, AZT (3'-azido-2'-3'-dideoxythimidine, azidothymidine), 2',3'-dideoxyinosine (Didanosine), 2',3'-dideoxycytidine (Zalcitabine) and 2-amino-9-((2-hydroxyethoxy)methyl)-1H-purin-6(9H)-one (Acyclovir). Nucleoside phosphonates can also be nucleoside analogues.

The term 'glycosyl phosphate' is understood to mean a phosphorylated glycosyl residue. A 'glycosyl' is a compound with a functional group which has been derived from a sugar by removing the hemiacetal hydroxyl group. Examples of glycosyl-1-phosphates include: glucose-1-phosphate, mannose-1-phosphate, galactose-1-phosphate, 2-N-acetyl-glucosamine-1-phosphate, 6-deoxygulose-1-phosphate, 2-N-acetyl-galactosamine-1-phosphate, D-fucose-1-phosphate and L-fucose-1-phosphate; in each case in the α- or β-configuration on the anomeric centre (with mannose there is only the α form).

The term 'alkyl' comprises saturated aliphatic groups including straight-chain alkyl groups (for example methyl, ethyl, propyl, butyl, pentyl, hexyl, heptyl and octyl), branched-chain alkyl groups (for example isopropyl, tert-butyl, isobutyl), cycloalkyl (for example alicyclic) groups (for example cyclopropyl, cyclopentyl, cyclohexyl, cycloheptyl, cyclooctyl), alkyl-substituted cycloalkyl groups and cycloalkyl-substituted alkyl groups. 'Alkyl' includes further alkyl groups which comprise oxygen, nitrogen, sulphur or phosphorous atoms which replace one or more carbon atoms of the hydrocarbon structure. The term 'alkyl' also encompasses both unsubstituted alkyls and substituted alkyls, wherein the latter are based on alkyl residues which comprise substituents that replace a hydrogen atom on one or more carbon atoms of the hydrocarbon structure. For example such substituents can contain: alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl or an aromatic or heteroaromatic residue. Cycloalkyls can be substituted further, for example with the substituents named above. An 'alkylaryl' or 'aralkyl' residue is an alkyl which is substituted with an aryl (for example phenylmethyl (benzyl)). 'Alkyl' also includes side chains of natural and unnatural amino acids.

'Aryl' is understood to mean groups with aromaticity, including 5- and 6-membered aromatic individual ring groups which may contain zero to four heteroatoms as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine and pyrimidine, and the like. Furthermore, the term 'aryl' includes multicyclic, (for example tricyclic, bicyclic) aryl groups, for example naphthalene, benzoxazole, benzodioxazole, benzothiazole, benzoimidazole, benzothiophene, methylene dioxyphenyl, quinoline, isoquinoline, napthridine, indole, benzofuran, purine, benzofuran, deazapurine or indolizine. 'Aryl' is also understood to mean aryl groups which comprise heteroatoms in the ring structure ('heteroaryls'). The aromatic ring can be substituted on one or more ring positions. Aryl groups can also be fused or bridged with alicyclic or heterocyclic rings which are not aromatic, in such a way that a multicyclic system is formed (for example tetralin, methylene dioxyphenyl).

The nucleophile is preferably selected from the group consisting of phosphate, pyrophosphate, glycosyl phosphate, nucleoside, nucleoside monophosphate, nucleoside diphosphate, nucleoside triphosphate nucleoside analogue, nucleoside monophosphate analogue, nucleoside diphosphate analogue, nucleoside triphosphate analogue and α-deprotonated glycosyl, or salts thereof.

In the case of phosphate, nucleoside diphosphates for example can be produced, and in the case of pyrophosphate nucleoside triphosphates for example can be produced, these representing highly significant compounds. The use of glycosyl phosphates leads to XDP sugars, which also constitute a very significant compound class.

Dinucleoside polyphosphates corresponding to the above formula (V) are produced as a product with the use of nucleoside mono-, di- and triphosphate as a nucleophile. Dinucleotides such as NAD or FAD can be produced by using the corresponding nucleoside monophosphates as a nucleophile. Compounds such as diadenosine tetraphosphate can be produced with the use of adenosine triphosphate (ATP). For example, in addition to a 5'-5' linking of the nucleosides a 5'-3' or 3'-3' bridging of the nucleosides by the phosphate groups is also possible. Only the starting materials used must be correspondingly selected in that instance.

For example the use of α-deprotonated glycosyl as a nucleophile leads to sugar nucleotide bioconjugates. It is easily evident to the person skilled in the art that phosphonates analogous to the nucleoside compounds above can also be produced using the method according to the invention. Unless expressly stated here otherwise, the corresponding phosphonates are to be included if reference is made herein to nucleoside compounds.

It is particularly advantageous if the nucleophile is used in excess to form the compound corresponding to formula (II). The molar ratio of nucleophile to compound (II) is particularly preferably >1.2:1, preferably ≥1.5:1, more preferably ≥1.7:1, ≥1.9:1, ≥2.0:1, ≥2.5:1 or ≥2.8:1. The molar ratio of nucleophile to compound (II) is particularly preferably 2.0-4.0 and most preferably 2.0-3.0. As used herein 'molar ratio' is understood to be the molar ratio of the compounds to one another. A molar ratio of 1.2:1 therefore can mean, for example, 1.2 mol of nucleophile to 1.0 mol of compound (II) or, for example, 2.4 mol of nucleophile to 2.0 mol of compound (II), etc. If the term 'equivalent' is used here it is also based on stoichiometric ratios and means molar equivalent. If 2 equivalents of compound (II) are added to 1 equivalent of a nucleophile, this means that the molar ratio of the compounds to one another is 1:2.

In a further preferred embodiment of the invention the nucleophile is dried in the solvent before the addition of compound (II), wherein an activated molecular sieve is preferably used, particularly preferably an activated molecular sieve with a pore width of 4 Å.

The term 'molecular sieve' refers to natural and synthetic zeoliths which have a high adsorption capacity for gases, steams and dissolved substances of specific molecular sizes. Molecular sieves make it possible to separate molecules in accordance with size, for example the separation of water from organic solvents. Molecular sieves have a large inner surface and uniform pore diameters which are approximately the size of the diameter of molecules. The mean pore width is often given in angstrom units, where 1 angstrom corresponds to $10^{-10}$ m. The term 'activated molecular sieve' refers to molecular sieves which, prior to use, have been set to a state which allows them to bind to as many target molecules as possible, for example water. For example a molecular sieve can be activated by being exposed to a suitable temperature (for example hot air blower, 15 minutes) under simultaneously reduced pressure. Activation procedures are known to the person skilled in the art and are also routinely specified by the manufacturer. The activated molecular sieve is stored in an inert gas atmosphere, for example in a nitrogen gas atmosphere.

It has proven to be advantageous if the solution is dried from the nucleophile and the solvent for at least 0.25 h, preferably at least 0.5 h, more preferably at least 0.75 h and particularly preferably at least approximately 1 h before compound (II) is added. The invention is not limited to the above specifications. In particular longer drying times, for example of at least 2, 3, 4 or 5 hours can be advantageous or expedient. The main thing is to achieve drying which is as complete as possible, i.e. free from water. If necessary, the person skilled in the art can easily ascertain from case to case how he might have to adjust the relevant conditions, for example duration of drying, size of the molecular sieve used, etc., by carrying out routine tests as required.

In a particularly preferred embodiment the method comprises the following steps:
a) dissolving and drying the nucleophile in the non-aqueous solvent over an activated molecular sieve, preferably over an activated molecular sieve with a pore width of 4 Å, for at least approximately 1 h, and
b) adding compound (II) to the dried solution produced in a), wherein the molar ratio of the nucleophile to compound (II) is >1.2:1, preferably ≥1.5:1, more preferably ≥1.7:1, ≥1.9:1, ≥2.0:1, ≥2.5:1 or ≥2.8:1, more preferably 2.0-4.0 and particularly preferably 2.0-3.0.

The combination of (1) the mixing sequence provided according to the invention, namely first production of a dry nucleophile solution, (2) the use of an activated molecular sieve for the drying and (3) the use of a molar ratio between the nucleophile and compound (II) of more than 1.2:1 has proven to be particularly advantageous for producing greater yields of the target compounds relatively simply and with a comparatively low expenditure of time.

In a particularly preferred embodiment of the method according to the invention the nucleoside in compound (II) is selected from the group consisting of adenosine, guanosine, cytidine, thymidine, uridine, deoxyadenosine, deoxyguanosine, inosine, deoxycytidine, deoxyuridine, deoxythymidine, 2-thiocytidine, $N^4$-acetyl-cytidine, 2'-O-methyl-cytidine, 3-methyl-cytidine, 5-methyl-cytidine, 2-thiouridine, pseudouridine, dihydrouridine, 5-(carboxyhydroxymethyl)-uridine, 5-carboxymethylaminomethyl-uridine, 5-methylaminomethyl-uridine, 5-methoxy-carbonylmethyl-uridine, 5-methoxy-uridine, ribo-thymidine, 1-methyl-adenosine, 2-methyl-adenosine, $N^6$-methyl-adenosine, inosine, 1-methyl-inosine, guanosine, $N^2$-2,2-dimethyl-guanosine, $N^2$-2-methyl-guanosine, $7^+$-methyl-guanosine, and 2'-O-methyl-guanosine.

Nucleosides or nucleoside analogues as well as nucleoside mono-, di- and triphosphates or mono-, di- and triphosphates of nucleoside analogues can be used both in the compound according to formula (II) and in the nucleophile or as a nucleophile. For example a nucleoside used as a nucleophile can be one of the nucleosides mentioned above for compound (II). If a nucleophile nucleoside or nucleophile nucleoside analogue, i.e. a nucleoside or nucleoside analogue provided as a nucleophile, or the phosphates thereof is used, the nucleoside in compound (II) and the nucleophile nucleoside can be the same or else different, but are preferably different.

The non-aqueous solvent is preferably an organic solvent which is selected from dimethylformamide (DMF), dimethylsulphoxide (DMSO), acetonitrile, tetrahydrofuran (THF), dichloromethane (DCM), ether (apart from diethyl ether), or any mixtures thereof. It is particularly advantageous if, in the case of glycosyl phosphate as a nucleophile, the non-aqueous solvent is selected from dimethylformamide and dimethylsulphoxide or a mixture thereof, and in the case of phosphate or pyrophosphate as a nucleophile is selected from dimethylformamide, dimethylsulphoxide, dichloromethane, acetonitrile, tetrahydrofuran and ether (apart from diethyl ether), or a mixture thereof. A mixture as used herein is understood to mean any composition of two or more of the named compounds in any mixing ratios.

In a particularly preferred embodiment the method is carried out under a suitable inert gas, for example nitrogen gas.

For example the products obtained can be cleaned by RP silica gel column chromatography.

The invention will be explained hereinafter in greater detail with reference to practical examples and FIG. 1.

Figure 1:
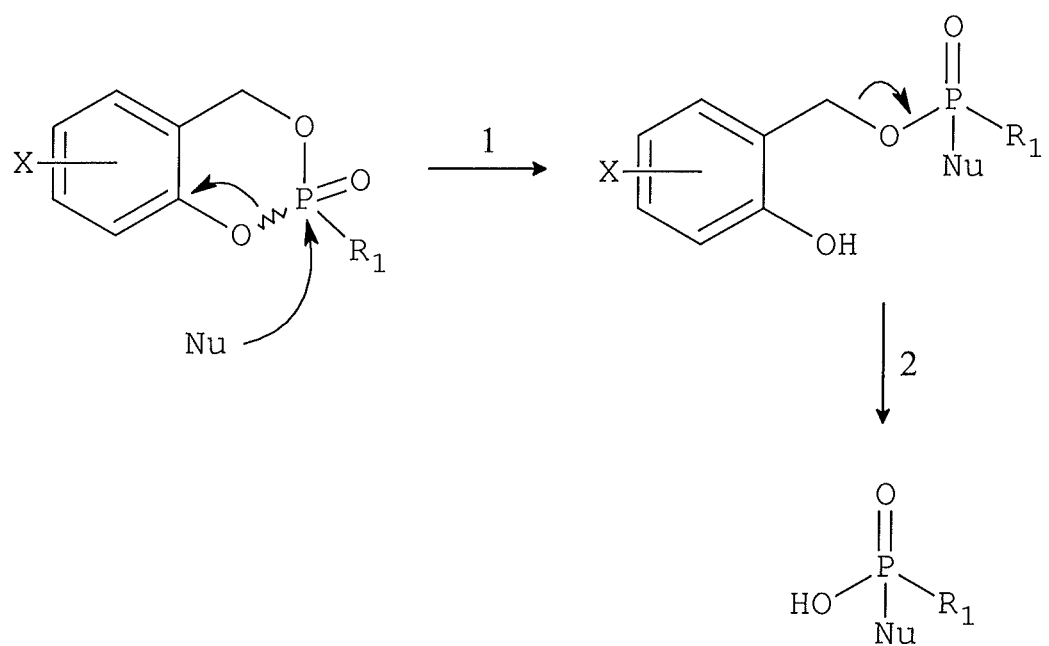
FIG. 1 is a schematic view of the assumed reaction mechanism underlying the method according to the invention.

FIG. 1 is a schematic view of the reaction mechanism which presumably takes place during the method according to the invention. A nucleophile Nu nucleophilically attacks the phosphorous atom of the neutral cycloSal-phosphate triester. The phenylphosphate ester bond of the cycloSal-compound dissolves and the nucleophile bonds covalently to the phosphate atom (step 1). The conjugate is then released from the nucleotide and the nucleophile by a spontaneous reaction (step 2).

Figure 2A:
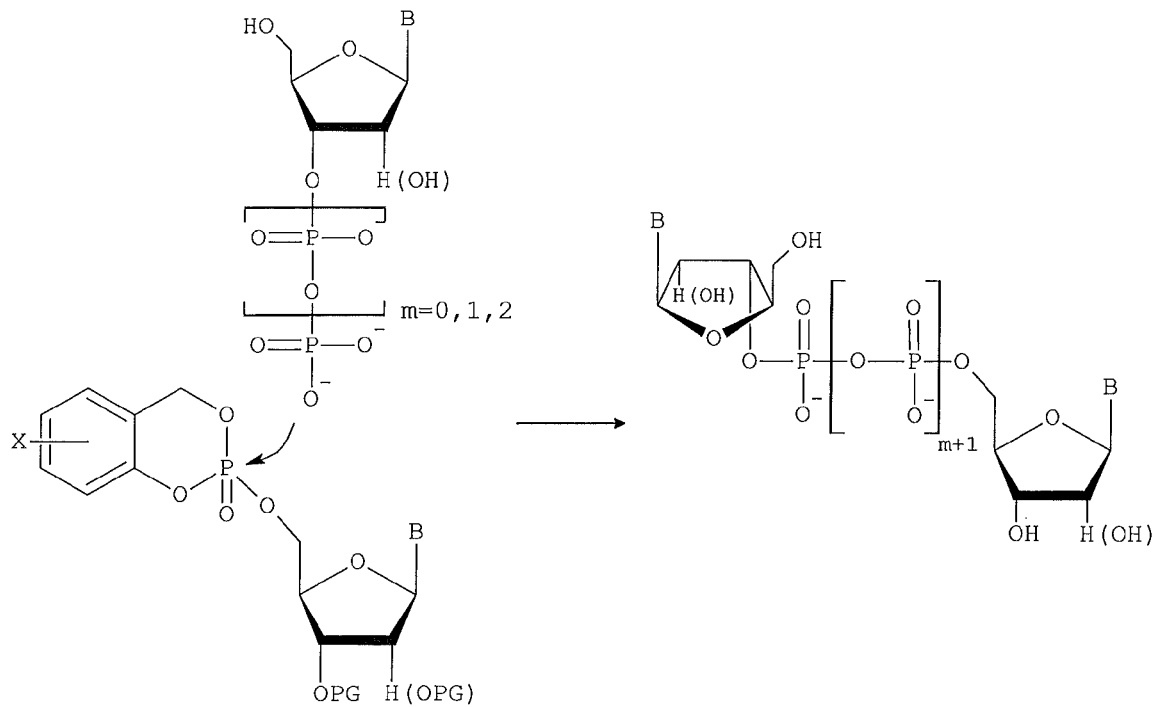
FIG. 2 is a schematic view of the production of exemplary dinucleoside polyphosphates with 3'-5' linking of the nucleosides via the phosphate groups (FIG. 2A) and with 3'-3' linking of the nucleosides via the phosphate groups (FIG. 2B). PG=protective group, H(OH)=H or OH, H(OPG)=H or OPG, B=nucleobase.
Figure 2B:
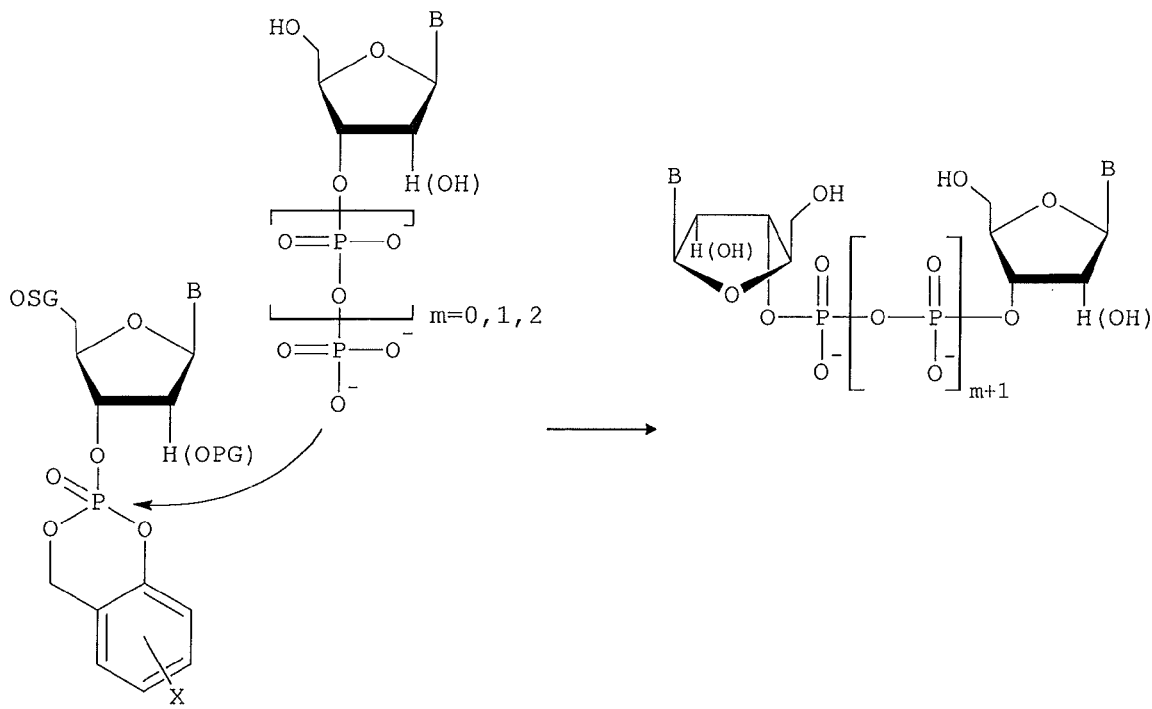

FIG. 2 is a schematic and exemplary view of the production of dinucleoside polyphosphates with 3'-5' linking of the nucleosides via the phosphate groups (FIG. 2A) and with 3'-3' linking of the nucleosides via the phosphate groups (FIG. 2B). If the nucleoside in compound (II) is linked to the phosphate group of the cyclosaligenyl residue via the 5'-hydroxyl group and the phosphate group(s) in the nucleoside mono-, di- or triphosphate used as a nucleophile is/are positioned on the 3'-C atom, dinucleoside polyphosphates with 3'-5' linking are produced (FIG. 2A). If the nucleoside in compound (II) is linked to the phosphate group of the cyclosaligenyl residue via the 3'-hydroxyl group and the phosphate used as a nucleophile is/are positioned on the 3'-C atom, dinucleoside polyphosphates with 3'-3' linking are produced (FIG. 2B). Different protective groups (PGs) can be used, for example acetyl groups. The nucleosides comprised by compound (II) or the nucleophile can be the same or different.

EXAMPLE 1

Production of Nucleoside Diphosphate Pyranoses

A schematic and simplified illustration of the synthesis of nucleoside diphosphate pyranoses is given below.

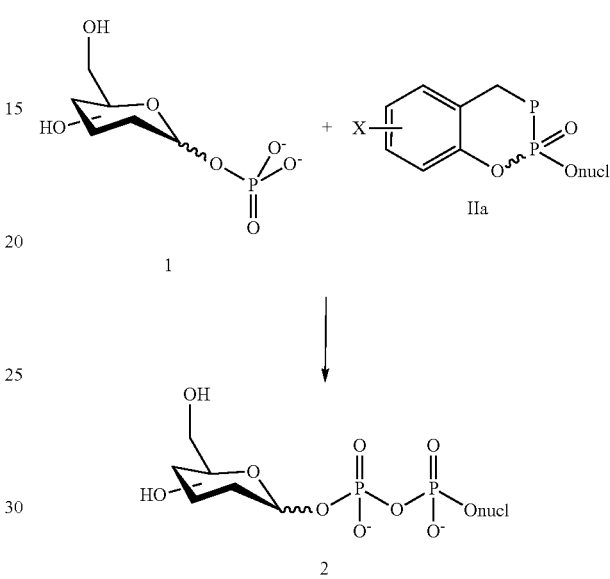

Nucleoside diphosphate pyranoses can generally be obtained by following the instructions below:

The reaction is carried out under nitrogen as an inert gas in order to exclude moisture. 2 equivalents of the respective glycosyl-1-phosphate 1 (in the form of the triethyl ammonium salt), which has been dried previously for a number of hours under vacuum), are dissolved in abs. DMF and left over an activated molecular sieve (4 Å) for 1 h. 1 equivalent of the cycloSal-nucleoside monophosphate IIa, dissolved in abs. DMF, is then slowly added dropwise. The reaction mixture is stirred for 24 h at room temperature and the reaction is monitored by thin-film chromatography (dichloromethane/methanol 9:1, v/v). Once the triester IIa has reacted completely the solvent is removed under vacuum. The residue is absorbed in ethyl acetate and extracted with water. The aqueous phase is freeze-dried. The sugar nucleotide 2 obtained after freeze-drying is absorbed in a mixture of 3 mL of water, 7 mL of methanol and 1 mL of triethylamine and stirred overnight at room temperature. After renewed freeze-drying the raw product is cleaned by RP-18 silica gel column chromatography with water as an eluent. Product fractions are detected by thin-film chromatography with a mixture of isopropanol and 1 N of ammonium acetate solution (2:1, v/v).

The instructions above also apply to the production of corresponding phosphonate compounds.

EXAMPLE 1.1

Synthesis of Cytidine Diphosphate-α-D-Mannose

The reaction was carried out under nitrogen as an inert gas in order to exclude moisture. 110 mg (0.20 mmol) of 2,3,4,6-tetra-O-acetyl-α-D-mannopyranosyl-1-phosphate (in the form of the triethyl ammonium salt), which had been dried previously for a number of hours under vacuum), were dissolved in 3 mL of abs. DMF and left over an activated molecular sieve (4 Å) for 1 h. 55 mg (0.10 mmol) of 5-nitro-cycloSal-N⁴—Ac-2',3'-O-accytidine monophosphate, dissolved in 2 mL of abs. DMF, were then slowly added dropwise. The reaction mixture was stirred for 24 h at room temperature and monitored by thin-film chromatography (dichloromethane/methanol 9:1). Once the triester had reacted completely the solvent was removed under vacuum. The residue was absorbed in ethyl acetate and extracted with water. The aqueous phase was lyophilised. The sugar nucleotide obtained after freeze-drying was absorbed in a mixture of 20 mL of methanol, 9 mL of water and 3 mL of triethylamine and stirred overnight at room temperature. After renewed freeze-drying the raw product was cleaned by RP-18 silica gel column chromatography with water as an eluent. Product fractions were detected by thin-film chromatography with a mixture of isopropanol and 1 N of ammonium acetate solution (2:1, v/v).

Yields: 62.0 mg (0.08 mmol, 86%) of a colourless solid

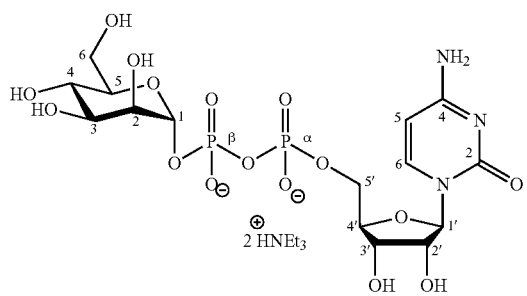

EXAMPLE 2

Production of Nucleoside Polyphosphates

A schematic and simplified illustration of the synthesis of nucleoside polyphosphates is given below:

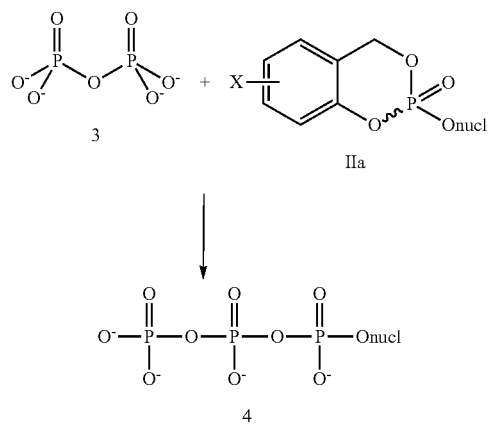

Nucleoside polyphosphates can generally be produced by following the instructions below:

The phosphate 3 (2.2 equiv.) used as a nucleophile, for example pyrophosphate, is first dried (in the form of its tetra-n-butyl ammonium salt) under an oil-pump vacuum and then further under a nitrogen atmosphere over a 4 Å molecular sieve in abs. DMF. Compound IIa, in this instance for example a corresponding 5-nitrosaligenyl-nucleoside monophosphate (1.0 equiv.) (for example 5-NO₂-cycloSal-3'-O-acetyl-2'-deoxythymidine monophosphate), dissolved in anhydrous DMF, is then slowly added dropwise. The reaction mixture is stirred overnight at room temperature. Once the reaction has finished the solvent is removed under reduced pressure and the residue is extracted with ethyl acetate and water. The combined aqueous phases are freeze-dried. The residue is optionally stirred in a methanol/water/triethylamine mixture (7:3:1) for 6 hours at room temperature in order to remove acetyl protecting groups on the nucleoside, then diluted with water and freeze-dried. The deprotected raw product is converted into the corresponding ammonium salt by ion exchange (Dowex 50X8, NH₄⁺ form) and freeze-dried again. The residue is cleaned by RP—C₁₈ silica gel chromatography (LiChroprep 25-40 μm, Merck, Darmstadt, Germany) with water as an eluent. After subsequent freeze-drying the nucleoside polyphosphates 4, for example a corresponding nucleoside triphosphate, are obtained as a colourless solid.

The instructions above also apply to the production of corresponding phosphonate compounds.

EXAMPLE 2.1

Synthesis of 2'-Deoxythymidine-5'-Triphosphate 175 mg (0.26 mmol) of freshly prepared tris-(tetra-n-butyl ammonium)hydrogen pyrophosphate were first dried under an oil-pump vacuum and then further under a nitrogen atmosphere over a 4 Å molecular sieve in abs. DMF. 60 mg (0.12 mmol) of 5-nitro-cycloSal-3'-O-acetyl-dTMP, dissolved in anhydrous DMF, were then slowly added dropwise to this solution. The reaction mixture was stirred overnight at room temperature. Once the reaction had finished the solvent was removed under reduced pressure and the residue was extracted with ethyl acetate and water. The combined aqueous phases were freeze-dried. The residue was stirred in a methanol/water/triethylamine mixture (7:3:1) for 6 hours at room temperature in order to remove the acetyl protecting group on the nucleoside, then diluted with water and freeze-dried. The deprotected raw product was converted into the corresponding ammonium salt by ion exchange (Dowex 50X8, NH₄⁺ form) and freeze-dried again. The residue was cleaned by RP—C₁₈ silica gel chromatography (LiChroprep 25-40 μm, Merck) with water as an eluent. After subsequent freeze-drying the desired product was obtained as a colourless solid at a yield between 50 and 80%.

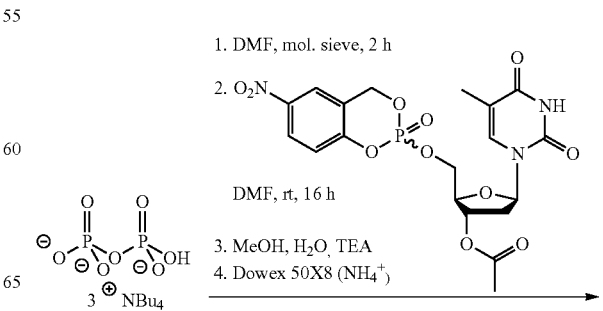

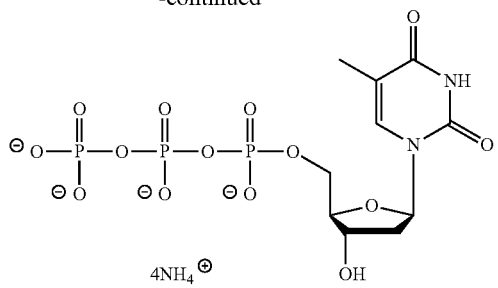

EXAMPLE 3

Production of Nucleoside Monophosphate Glycosides

A schematic and simplified illustration of the synthesis of nucleoside monophosphate glycosides is given below.

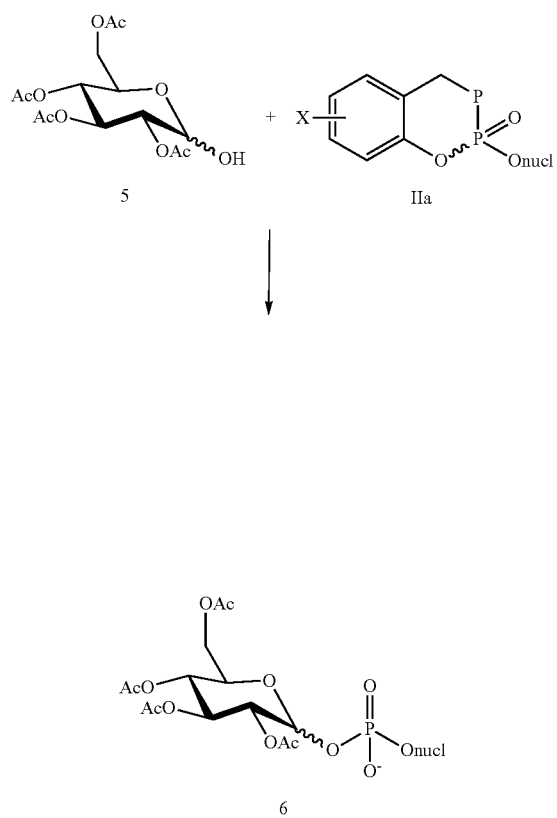

A 2,3,4,6-tetra-O-acetylglycoside (4.0 equiv.) 5 is first dried under an oil-pump vacuum and then further under a nitrogen atmosphere over a 4 Å molecular sieve in dichloromethane (DCM). 4.0 equivalents of NaH (60%) are then added in portions to this solution which is then stirred at room temperature for 10 minutes. A corresponding compound (IIa), for example a corresponding 5-nitrosaligenyl nucleoside monophosphate (1.0 equiv.) (for example 5-NO$_2$-cycloSal-3'-O-acetyl-deoxythymidine monophosphate), dissolved in anhydrous DCM, is then added dropwise to the resultant glycosyl-1-oxide. The reaction mixture is stirred for 2 hours at room temperature. Once the reaction has finished the culture is extracted with ethyl acetate and water and the combined aqueous phases are freeze-dried. A methanol/water/triethylamine mixture (7:3:1) is added to the residue and stirred for 6 hours at room temperature in order to remove the acetyl protecting groups, then diluted with water and freeze-dried again. The deprotected raw product is cleaned by RP—C$_{18}$ silica gel chromatography (LiChroprep 25-40 µm, Merck, Darmstadt, Germany) with water as an eluent. After subsequent freeze-drying the nucleotide glycoside 6 is obtained as a colourless solid.

EXAMPLE 4

Production of Dinucleoside Polyphosphates

The production of two different dinucleoside polyphosphates of the structure Np$_n$N' is described below by way of example, wherein in this instance the nucleosides N are uridine and adenosine and the nucleosides N' are thymidine in each case. The nucleosides are linked via two phosphate groups in the case of Up$_2$T and via four phosphate groups in the case of Ap$_4$T.

EXAMPLE 4.1

Synthesis of Up$_2$T 112 mg (0.2 mmol) of freshly prepared (tetra-n-butyl ammonium)hydrogen uridine monophosphate were first dried under an oil-pump vacuum and then further under a nitrogen atmosphere over a 4 Å molecular sieve in abs. DMF. This solution was then slowly added dropwise to 50 mg (0.1 mmol) of 5-nitro-cycloSal-3'-O-acetyl-dTMP, dissolved in anhydrous DMF. The reaction mixture was stirred overnight at room temperature. Once the reaction had finished the solvent was removed under reduced pressure and the residue was extracted with ethyl acetate and water. The combined aqueous phases were freeze-dried. The residue was stirred in a methanol/water/triethylamine mixture (7:3:1) for 6 hours at room temperature in order to remove the acetyl protecting group, then diluted with water and freeze-dried. The deprotected raw product was converted into the corresponding ammonium salt by ion exchange (Dowex 50X8, NH$_4^+$ form) and freeze-dried again. The residue was cleaned by RP—C$_{18}$ silica gel chromatography (LiChroprep 25-40 µm, Merck) with water as an eluent. After subsequent freeze-drying the desired product was obtained as a colourless solid at a yield of 60%.

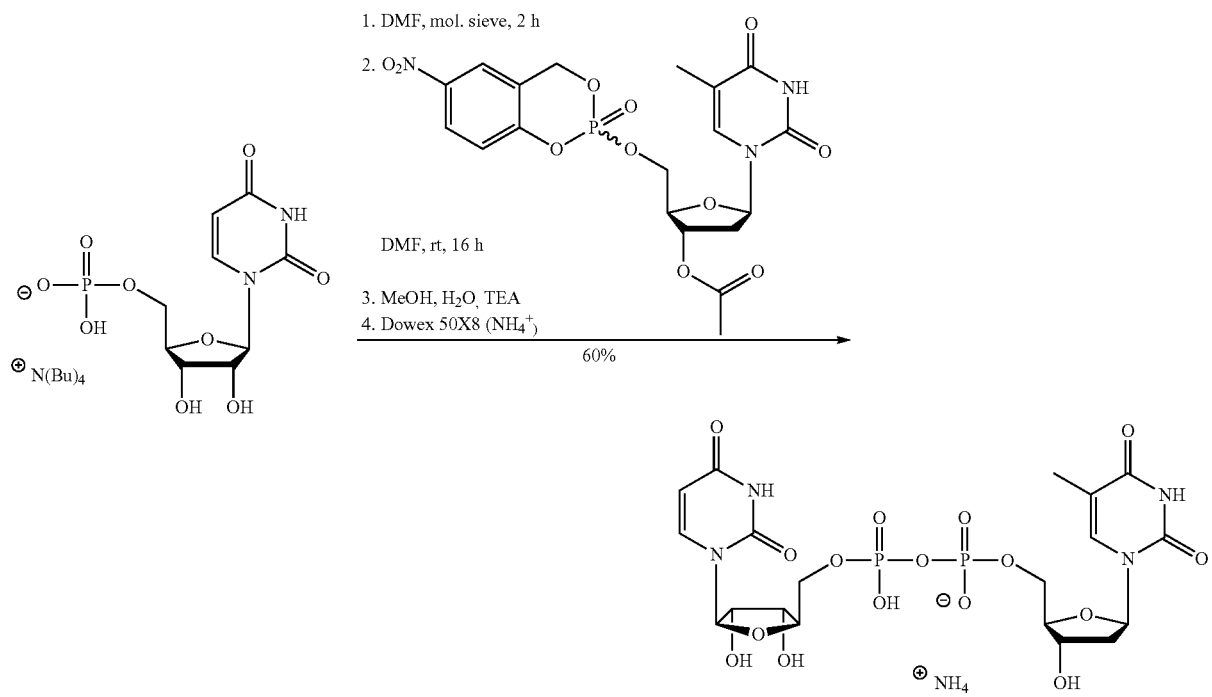

EXAMPLE 4.2

Synthesis of Ap$_4$T 300 mg (0.24 mmol) of freshly prepared tris-(tetra-n-butyl ammonium)hydrogen adenosine triphosphate were first dried under an oil-pump vacuum and then further under a nitrogen atmosphere over a 4 Å molecular sieve in abs. DMF. This solution was then slowly added dropwise to 60 mg (0.12 mmol) of 5-nitro-cycloSal-3′-O-acetyl-dTMP, dissolved in anhydrous DMF. The reaction mixture was stirred over night at room temperature. Once the reaction had finished the solvent was removed under reduced pressure and the residue was extracted with ethyl acetate and water. The combined aqueous phases were freeze-dried. The residue was stirred in a methanol/water/triethylamine mixture (7:3:1) for 6 hours at room temperature in order to remove the acetyl protecting group, then diluted with water and freeze-dried. The deprotected raw product was converted into the corresponding ammonium salt by ion exchange (Dowex 50X8, NH$_4^+$ form) and freeze-dried again. The residue was cleaned by RP—C$_{18}$ silica gel chromatography (LiChroprep 25-40 μm, Merck) with water as an eluent. After subsequent freeze-drying the desired product was obtained as a colourless solid at a yield of 55%.

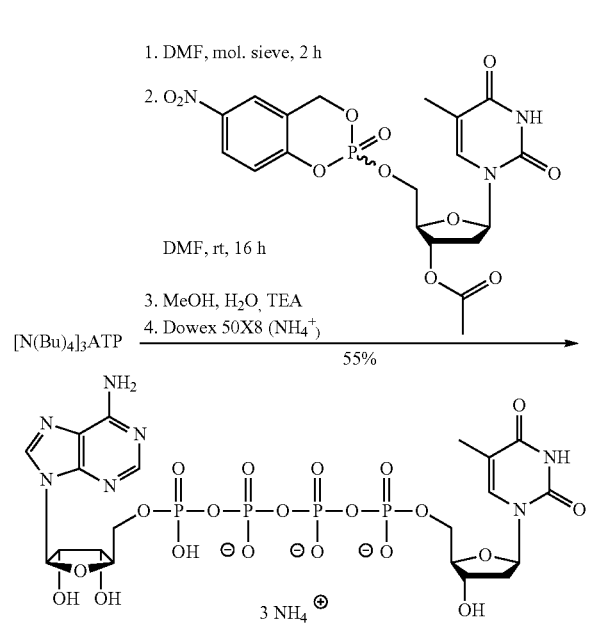

The invention claimed is:
1. A method for producing compounds of the general formula (I):

or salts thereof, $R_1$ being Onucl or nucl, wherein nucl is a nucleoside or nucleoside analogue, and wherein $R_2$ is glycosly phosphate, comprising the steps of:

first dissolving a nucleophile identical to $R_2$ or comprising $R_2$ in a non-aqueous solvent, drying the nucleophile in the non-aqueous solvent, and subsequently adding a compound corresponding to the general formula (II)

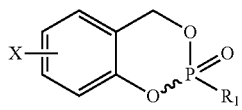
(II)

to the solution such that the molar ratio of nucleophile to compound (II) is >1.2:1, wherein $R_1$ is as defined above and the compound (II) can be substituted once or more with X, and wherein X is an electron acceptor.

2. The method according to claim 1, wherein, a plurality of substituents X is present, X being selected independently from the group consisting of H, OMe, $MeSO_2$, ketone, formyl, ester, COOH, $NO_2$ and halogen, wherein Me stands for methyl.

3. The method according to claim 1, wherein the nucleophile is dried over an activated molecular sieve.

4. The method according to claim 1, comprising the following steps:

a) dissolving and drying the nucleophile in the non-aqueous solvent over an activated molecular sieve for at least approximately 1 h, and b) adding compound (II) to the dried solution produced in a), wherein the molar ratio of the nucleophile to compound (II) is >1.2:1.

5. The method according to claim 1, wherein nucl is selected from the group consisting of adenosine, guanosine, cytidine, thymidine, uridine, deoxyadenosine, deoxyguanosine, inosine, deoxycytidine, deoxyuridine, deoxythymidine, 2-thiocytidine, $N^4$-acetyl-cytidine, 2'-O-methyl-cytidine, 3-methyl-cytidine, 5-methyl-cytidine, 2-thiouridine, pseudouridine, dihydrouridine, 5-(carboxyhydroxymethyl)-uridine, 5-carboxymethylaminomethyl-uridine, 5-methylaminomethyl-uridine, 5-methoxy-carbonylmethyl-uridine, 5-methoxy-uridine, ribo-thymidine, 1-methyl-adenosine, 2-methyl-adenosine, $N^6$-methyl-adenosine, inosine, 1-methyl-inosine, guanosine, $N^2$-2,2-dimethyl-guanosine, $N^2$-2-methyl-guanosine, $7^+$-methyl-guanosine, and 2'-O-methyl-guanosine.

6. The method according to claim 1, wherein the non-aqueous solvent is an anhydrous organic solvent.

7. The method according to claim 1, wherein the non-aqueous solvent is selected from dimethylformamide and dimethylsulphoxide, or a mixture thereof.

8. The method according to claim 1, wherein the method is carried out under an inert gas atmosphere.

9. The method according to claim 1, wherein the molar ratio of nucleophile to compound (II) is 2.0-4.0.

10. The method according to claim 1, wherein the molar ratio of the nucleophile to compound (II) is 2.0-3.0 and the nucleophile is dried over an activated molecular sieve having a pore width of 4 Å.

* * * * *